United States Patent
Lee (10) Patent No.: US 8,715,650 B2
(45) Date of Patent: May 6, 2014

(54) BATHING COMPOSITION AND METHOD FOR PREPARING SAME

(76) Inventor: Dong-Joo Lee, Seoul (KR)

(*) Notice: Subject to any disclaimer, the term of this patent is extended or adjusted under 35 U.S.C. 154(b) by 0 days.

(21) Appl. No.: 13/702,103

(22) PCT Filed: Jun. 10, 2011

(86) PCT No.: PCT/KR2011/004269
§ 371 (c)(1),
(2), (4) Date: Dec. 5, 2012

(87) PCT Pub. No.: WO2011/155792
PCT Pub. Date: Dec. 15, 2011

(65) Prior Publication Data
US 2013/0071376 A1    Mar. 21, 2013

(30) Foreign Application Priority Data

Jun. 11, 2010 (KR) .................... 10-2010-0055287
Jun. 10, 2011 (WO) ................ PCT/KR2011/004269

(51) Int. Cl.
*A61K 36/899* (2006.01)
*A61K 35/74* (2006.01)

(52) U.S. Cl.
USPC .......................... 424/114; 435/170

(58) Field of Classification Search
USPC .......................... 424/114; 435/170
See application file for complete search history.

(56) References Cited

U.S. PATENT DOCUMENTS

2008/0131384 A1* 6/2008 Maeda et al. .............. 424/62

FOREIGN PATENT DOCUMENTS

| JP | 403044317 | * | 2/1991 | ............ A61K 7/50 |
| JP | 05-140597 | A | 8/1993 | |
| KR | 10-0512148 | B1 | 9/2005 | |
| KR | 2008039573 | * | 11/2006 | ............ A61K 8/97 |
| KR | 20088079743 | * | 2/2007 | ............ A61K 36/60 |
| KR | 2008090660 | * | 4/2007 | ............ C11D 9/04 |
| KR | 10-2008-0073466 | A | 8/2008 | |
| KR | 10-08866109 | B1 | 2/2009 | |

* cited by examiner

*Primary Examiner* — Karen Cochrane Carlson
*Assistant Examiner* — Jennifer M Tichy
(74) *Attorney, Agent, or Firm* — AKC Patents LLC; Aliki K. Collins

(57) ABSTRACT

The present invention relates to a composition for bath additives characterized in that the composition is obtained by a process comprising: subjecting herbal materials to liquid phase fermentation with *Bacillus subtilis* to obtain a culture, the herbal materials comprising 10% to 25% by weight of *Zizania latifolia*, 10% to 20% by weight of *Artemisia capillaries*, 5% to 15% by weight of *Houttuynia cordata*, 1% to 20% by weight of *Saururus chinensis*, 1% to 15% by weight of *Leonurus sibiricus*, 1% to 15% by weight of *Angelica gigas*, 1% to 15% by weight of *Coix lachryma-jobi*, 1% to 10% by weight of *Plantago asiatica* and 1% to 10% by weight of *Rhododendron brachycarpum*, based on a total dry weight of the herb materials; separating sludge from the resulting culture; and drying, sterilizing and pulverizing the sludge.

9 Claims, 2 Drawing Sheets

Before bathing

After one time bathing

Fig.1

Before bathing    After bathing

Fig.2

Before bathing    After bathing

Fig.3

Before bathing    After one time bathing

BATHING COMPOSITION AND METHOD FOR PREPARING SAME

TECHNICAL FIELD

The present invention relates to a composition for bath additives for body type correction and immunological enhancement, and to a process for preparing the same.

BACKGROUND

Due to several factors such as irregular meals, artificial air-conditioning/heating, various stresses from social life, environmental pollution, =frequent washing for make-up removal, and natural skin aging, modern people are easily exposed to skin injuries such as deficiency of essential minerals and amino acids for maintaining homeostasis of body, skin drying, and keratogenesis. Therefore, efforts to maintain the homeostasis of body and protect and improve the skin are requested.

As half bath, aroma bath and the like have been recently known, attention to bath therapies which are helpful to the health is increased. Such bath therapies are known to provide noticeable effects from make-up effect to the prevention and treatment of diseases without special side-effect.

Particularly, bath therapies using bath additives having various medicinal ingredients are drawing a great interest because of their effects. The bath additives refer to substances placed and used in a bath for the purpose of prevention of diseases and alleviation of symptoms, protection and washing of skins, and recovery of fatigues. As bath additives, a bath crystal, a bath salt, a vegetable preparation, a milk bath, a paste preparation, a jelly preparation, bath oil, bath calcium, a bubble bath and the like are usually used depending on preparations, ingredients and effects.

The bath additives comprise mostly mineral and vegetable materials. Recently, development of the bath additives to provide oriental medicinal therapeutic effects using such herbs has been actively made. The bath additives using such herbs seem to derive from a traditional therapy of boiling medicinal herb materials and then exposing the resulting steam to a subject or dipping a whole body with the drug water. The bath additives using such herbs can be applied by various methods, for example, in washing a lesion or in dipping a whole body to a bath water containing the bath additives. Generally, the bathing is made as follows: The bath is filled with hot water; 50 to 100 g of herbal bath materials are placed and tied in cotton or cloth wrapper, and then brewed in a bath water. Subsequently, while herb water is properly brewed, a user takes a quick shower. The user enters the bath water when the temperature of the bath water is lowered to 36° C. to 38° C., dips the body for 15 to 20 minutes, and then comes out the bath, puts soap on the body, and rinses the body by raising a hydrostatic pressure.

However, when bathing is made using such herbs, a user has to purchase the herbs directly, brew them in hot water of the bath and then has a bath with the herbal bath water. As such, the bathing is very cumbersome and inconvenient. There is a limit to universalize it in an ordinary household. Conventional bath additives aim at providing effects of make-up or soothing a skin and alleviating dermatitis. Therefore, there is a need to develop functional bath additives having various therapeutic effects.

DISCLOSURE OF THE INVENTION

Technical Problem

Thus, in order to resolve the above mentioned problems, the purpose of the present invention is to provide a composition for bath additives having effects of body type correction and immunological enhancement by activating natural healing power using fermented medicinal herb ingredients, and a process for preparing the same.

Also, another purpose of the present invention is to provide a composition for bath additives which is very safe by removing inherent toxicity of medicinal herb materials and toxic substance such as pesticide residue by fermentation and which can be conveniently used by preparing them in powder type and diluting them in a bath water, and a process for preparing the same.

Technical Solution

In order to accomplish the above purpose, the present invention provides a composition for bath additives characterized in that the composition is obtained by a process comprising subjecting medicinal herb materials comprising 10 to 25% by weight of *Zizania latifolia*, 10 to 20% by weight of *Artemisia capillaries*, 5 to 15% by weight of *Houttuynia cordata*, 1 to 20% by weight of *Saururus chinensis*, 1 to 15% by weight of *Leonurus sibiricus*, 1 to 15% by weight of *Angelica gigas*, 1 to 15% by weight of *Coix lachryma-jobi*, 1 to 10% by weight of *Plantago asiatica* and 1 to 10% by weight of *Rhododendron brachycarpum*, based on the total dry weight of the above herb materials, to liquid phase fermentation with *Bacillus subtilis* which is anaerobic, to obtain a culture, separating sludge from the resulting culture, drying, sterilizing and pulverizing the sludge to give a pulverized sludge.

Also, the present invention provides a composition for bath additives characterized in that the composition is obtained by a process comprising: subjecting first medicinal herb materials comprising 10 to 25% by weight of *Zizania latifolia*, 10 to 20% by weight of *Artemisia capillaries*, 5 to 15% by weight of *Houttuynia cordata*, 1 to 20% by weight of *Saururus chinensis*, 1 to 15% by weight of *Leonurus sibiricus*, 1 to 15% by weight of *Angelica gigas*, 1 to 15% by weight of *Coix lachryma-jobi*, 1 to 10% by weight of Plantago asiatica and 1 to 10% by weight of *Rhododendron brachycarpum*, based on the total dry weight of the above first herb materials, to first liquid phase fermentation with *Bacillus subtilis* which is anaerobic, to obtain a culture, separating first sludge from the resulting culture, drying, sterilizing and pulverizing the sludge to give a pulverized sludge; mixing the pulverized sludge with second medicinal herb materials comprising 10 to 15% by weight of *Zizania latifolia*, 1 to 10% by weight of *Artemisia capillaries*, 1 to 10% by weight of *Houttuynia cordata*, 5 to 15% by weight of *Saururus chinensis*, 5 to 15% by weight of *Leonurus sibiricus*, 1 to 10% by weight of *Angelica gigas*, 3 to 12% by weight of *Coix lachryma-jobi*, 5 to 15% by weight of *Saliconia herbacea*, 1 to 10% by weight of *Plantago asiatica*, 5 to 15% by weight of *Achillea sibirica*, 5 to 15% by weight of *Rumex crispus*, 1 to 10% by weight of *Rhododendron brachycarpum* and 1 to 5% by weight of *Lithospermum erythrorhizon*, based on the total dry weight of the above second herb materials, in a weight ratio of 3:7 to 7:3, the second materials being in a powder state, subjecting the mixture to second liquid phase fermentation with *Aspergillus oryzae* which is leaven bacteria, and *Lactobacillus acidophilus* which is lactic acid bacteria, and separating second sludge from the resulting culture and drying the second sludge.

Further, the present invention provides a method for preparing a composition for bath additives comprising:
preparing medicinal herb materials comprising 10 to 25% by weight of *Zizania latifolia*, 10 to 20% by weight of *Arte-*

*misia capillaries*, 5 to 15% by weight of *Houttuynia cordata*, 1 to 20% by weight of *Saururus chinensis*, 1 to 15% by weight of *Leonurus sibiricus*, 1 to 15% by weight of *Angelica gigas*, 1 to 15% by weight of *Coix lachryma-jobi*, 1 to 10% by weight of *Plantago asiatica* and 1 to 10% by weight of *Rhododendron brachycarpum*, based on the total dry weight of the herb materials, mixing the herb materials, water and *Bacillus subtilis* which is anaerobic, and separating the first mixture to first liquid phase fermentation at a temperature of 30 to 40° C. for 50 to 100 days, and separating first sludge from the culture obtained from the liquid phase fermentation, drying, sterilizing and pulverizing the first sludge.

In addition, the process for preparing a composition for bath additives further comprises: mixing the pulverized sludge with second medicinal herb materials comprising 10 to 15% by weight of *Zizania latifolia*, 1 to 10% by weight of *Artemisia capillaries*, 1 to 10% by weight of *Houttuynia cordata*, 5 to 15% by weight of *Saururus chinensis*, 5 to 15% by weight of *Leonurus sibiricus*, 1 to 10% by weight of *Angelica gigas*, 3 to 12% by weight of *Coix lachryma-jobi*, 5 to 15% by weight of *Saliconia herbacea*, 1 to 10% by weight of *Plantago asiatica*, 5 to 15% by weight of *Achillea sibirica*, 5 to 15% by weight of *Rumex crispus*, 1 to 10% by weight of *Rhododendron brachycarpum* and 1 to 5% by weight of *Lithospermum erythrorhizon*, based on the total dry weight of the above second herb materials, in a weight ratio of 3:7 to 7:3, the second materials in a powder state, to prepare a second mixture; and subjecting the second mixture, water and *Aspergillus oryzae* which is leaven bacteria and *Lactobacillus acidophilus* which is lactic acid bacteria, to second liquid phase fermentation at a temperature of 26 to 30° C. for 50 to 70 days.

Advantageous Effects

The composition for bath additives according to the present application shows effects of body type correction and immunological enhancement by activating natural healing power using fermented medicinal herb ingredients, and a process for preparing the same.

Also, the composition for bath additives according to the present application is very safe by removing any inherent toxicity of medicinal herb materials and any toxic substance such as pesticide residue by fermentation, and can be conveniently used by preparing them in powder type and diluting them in a bath water. Accordingly, the present composition contributes greatly to universalize the use of the bath additives.

BEST MODE FOR CARRYING OUT THE INVENTION

The present invention relates to a composition for bath additives characterized in that the composition is obtained by a process comprising subjecting medicinal herb materials comprising 10 to 25% by weight of *Zizania latifolia*, 10 to 20% by weight of *Artemisia capillaries*, 5 to 15% by weight of *Houttuynia cordata*, 1 to 20% by weight of *Saururus chinensis*, 1 to 15% by weight of *Leonurus sibiricus*, 1 to 15% by weight of *Angelica gigas*, 1 to 15% by weight of *Coix lachryma-jobi*, 1 to 10% by weight of *Plantago asiatica* and 1 to 10% by weight of *Rhododendron brachycarpum*, based on the total dry weight of the above herbal materials, to liquid phase fermentation with *Bacillus subtilis* which is anaerobic, to obtain a culture, separating sludge from the resulting culture, drying, sterilizing and pulverizing the sludge to give a pulverized sludge.

In the composition for bath additives according to the present invention, *Bacillus subtilis* anaerobic microorganism, produces organisms (e.g., amino acid) in a state of strong reducibility and produces an anti-oxidizing substance through conversion of organisms into low-molecular form in a state of strong oxidizability. Some people may be sensitive to medicinal herb materials. In the present invention, fermenting the medicinal herb materials using anaerobic microorganisms is for the purpose of removing any inherent toxicity of the herb materials and any toxic substance such as pesticide residue. Also, new materials are produced by fermentation of such anaerobic microorganisms, and such new materials are considered to show excellent effects of immunological enhancement.

In the present composition for bath additives, the liquid phase fermentation is preferably performed at a temperature of 30 to 40° C. for 50 to 100 days. When the fermentation temperature deviates from the above range, proper fermentation is not made and it is likely to be decayed. When the fermentation period deviates from the above range, sufficient fermentation is not made or over-fermentation is made and thus, it is difficult to obtain the desired effect.

In the composition for bath additives, the medicinal herb materials may further comprise 1 to 10% by weight of *Saliconia herbacea*, 7 to 17% by weight of *Achillea sibirica*, 5 to 15% by weight of *Rumex crispus*, and 1 to 10% by weight of *Lithospermum erythrorhizon*, based on the total dry weight of the above herb materials.

The present invention relates to a composition for bath additives characterized in that the composition is obtained by a process comprising:

subjecting a first medicinal herb materials comprising 10 to 25% by weight of *Zizania latifolia*, 10 to 20% by weight of *Artemisia capillaries*, 5 to 15% by weight of *Houttuynia cordata*, 1 to 20% by weight of *Saururus chinensis*, 1 to 15% by weight of Leonurus sibiricus, 1 to 15% by weight of *Angelica gigas*, 1 to 15% by weight of *Coix lachryma-jobi*, 1 to 10% by weight of *Plantago asiatica* and 1 to 10% by weight of *Rhododendron brachycarpum*, based on the total dry weight of the above first herb materials, to liquid phase fermentation with *Bacillus subtilis* which is anaerobic, to obtain a culture, separating sludge from the resulting culture, drying, sterilizing and pulverizing the sludge to give a pulverized sludge;

mixing the pulverized sludge with second medicinal herb materials comprising 10 to 15% by weight of *Zizania latifolia*, 1 to 10% by weight of *Artemisia capillaries*, 1 to 10% by weight of *Houttuynia cordata*, 5 to 15% by weight of *Saururus chinensis*, 5 to 15% by weight of *Leonurus sibiricus*, 1 to 10% by weight of *Angelica gigas*, 3 to 12% by weight of *Coix lachryma-jobi*, 5 to 15% by weight of *Saliconia herbacea*, 1 to 10% by weight of *Plantago asiatica*, 5 to 15% by weight of *Achillea sibirica*, 5 to 15% by weight of *Rumex crispus*, 1 to 10% by weight of *Rhododendron brachycarpum* and 1 to 5% by weight of *Lithospermum erythrorhizon*, based on the total dry weight of the above second herb materials, in a weight ratio of 3:7 to 7:3, the second materials provided in a powder state, subjecting this mixture to liquid phase fermentation with *Aspergillus oryzae* which is leaven bacteria, and *Lactobacillus acidophilus* which is lactic acid bacteria, and separating sludge from the resulting culture and drying the sludge.

According to the present invention, the first and second fermentations are performed as mentioned above. The reason is that performing the second fermentation shows three times higher effects of a toxin discharge in the body, an immunological enhancement and a body type correction as compared with performing the first fermentation.

Details concerning the anaerobic microorganisms used in the present composition for bath additives are mentioned above.

When *Aspergillus oryzae*, a leaven bacteria used in the present invention, is purchased in the market, it is preferable to select the bacteria including a lot of yellowish green spore not old (within one month).

In the composition for bath additives, the liquid phase fermentation of the first medicinal herb materials is preferably performed at a temperature of 30 to 40° C. for 50 to 100 days, and the liquid phase fermentation of the second medicinal herb materials is preferably performed at a temperature of 26 to 30° C. for 50 to 70 days.

The criticality resulting from the condition of the liquid phase fermentation of the first medicinal herb materials is as mentioned above. When the fermentation temperature in the fermentation condition of the second medicinal herb materials deviates from the above range, proper fermentation is not made and it is decayed. When the fermentation period deviates from the above range, sufficient fermentation is not made or over-fermentation is made and thus, it is difficult to obtain the desired effect.

In the above composition for bath additives, the first medicinal herb materials comprise preferably 1 to 10% by weight of *Saliconia herbacea*, 7 to 17% by weight of *Achillea sibirica*, 5 to 15% by weight of *Rumex crispus*, and 1 to 10% by weight of *Lithospermum erythrorhizon*, based on the total dry weight of the first herb materials.

Below, the pharmaceutical effects of the herbal materials used in the composition for bath additives according to the present invention are described.

*Zizania latifolia* contains a large amount of protein, essential oil, ash, and trace element in its leaf, root and stem. Bathing in the bath water boiled with *Zizania latifolia* leads to unusual microorganisms not died even at 180° C. These microorganisms are known to be produced only when the body fluid touches the bath water boiled with *Zizania latifolia*. The microorganisms have the following functions: Even if water boiled with *Zizania latifolia* stands at room temperature for 3 to 4 months, it is not spoiled. In the case of bathing with this, all kinds of pathogenic bacterium, waste and toxin hidden deeply into the skin get out of the body, the body is exhilarated and well and also the skin is pearl-smooth. In addition, all kinds of skin diseases including eczema, scabies and furuncle are improved.

*Zizania latifolia* juice is effective as 100% natural functional skin lotion which is mysterious. That is, *Zizania latifolia* juice which is prepared by placing *Zizania latifolia* (*Zizania*; GoJanCho) in an extractor and then decocting it by unpressurized method for nine hours, has a natural fragrance which is similar to a corn tea, and also is very effective in removing toxin and waste in the skin, in whitening and moisturizing the skin, in delaying and improving the aging, and in itching.

*Artemisia capillaries* serve to activate the liver function as well as make the skin beautiful. That is, *Artemisia capillaries* contain a large amount of vitamin A, B1, B2 and C, calcium and iron powder. Vitamin A is presented basically as carotene ingredient, and thus gives resilience to the skin, is glossy, and assists skin beauty care. Also, *Artemisia capillaries* have a cleaning function for the liver due to their detoxifying properties, and thus they are also effective in treating jaundice. *Artemisia capillaries* are rich in various nutritive components and many active nutrients, vitamins and minerals. As such, toxic wastes such as lump, cholic acid and bilirubin contained in the bile get out of the body, and thus *Artemisia capillaries* have a function to clean the liver and help detoxifying it.

*Artemisia capillaries* have a component called capilarine, and thus they are known to take very effective role in facilitating bile secretion to activate the liver function. Also, *Artemisia capillaries* are effective in anorexia and fatigue feeling due to chronic hepatitis. When the physical strength of the youths and their grades at school are lowered due to B type hepatitis, *Artemisia capillaries* are effective in their strength improvement and their grades increase.

*Houttuynia cordata* is known to have an excellent pharmacological effect in beauty care and body weight control and in the removal of toxins from the body. *Houttuynia cordata* exhibits 40,000 times higher anti-inflammatory effects than sulfamine and contains "decanol acetate aldehyde" (fish flavor component) which is effective in the treatment of various inflammatory diseases. Further, this contains more "flavonoid" than ginkgo leaf and thus has an excellent blood purification effect. *Houttuynia cordata* is a rich repository of "potassium salt" which controls blood pressure. That is, it contains 25 times "jiamine" (vitamin B1) of ginseng, 3 times riboflavin of ginseng, 1.4 times niacin of ginseng, and 10 times alkaline component of ginseng.

*Saururus chinensis* is known to have excellent pharmacological effect in removing constipation and coprostasis. Their ingredients contain a large amount of quercitrin, isoquercitrin, flavonoid and the like. They help purging, detoxifying, and have diuretic actions. Also, they are effective in treating intoxication due to pollutant, ascites due to hepatic disease, nephritis, hydrops and the like. Further, they are effective in preventing and treating hepatic diseases and diabetes such as hepatitis and liver cirrhosis; hypertension and arteriosclerosis. Additionally, since they make the blood clean and wash the blood vessels cleanly, they are effective in preventing and treating hepatic diseases such as heart disease, hypertension and angina pectoris. That is, *Saururus chinensis* is effective in adipolysis, dieresis, diet, constipation, stercoral removal, hypertension, arteriosclerosis, beauty care, female disease, stamina increase, fatigue recovery, detoxification, water quality improvement, diabetes, renal disease, heart disease, ageing prevention, all kinds of female diseases.

*Leonurus sibiricus* is a biennial grass. In the first year, it grows as broad leaf in a state attached to soil similarly to spinach, and lives through the winter. In spring, the stem is originated and the leaf is developed. A raw juice of leaf is effective when losing one's appetite due to stomachache in summer. In autumn, flowers bloom from leaf. *Leonurus sibiricus* is frequently used in menstruation and postpartum as an essential drug for appetite improvement and various female diseases. This facilitates blood circulation, counteracts poisons, and is effective in female cryopathy. Further, this is effective in menstrual irregularity, stomachache after childbirth, metrorrhagia, neuralgia, endometritis, mazodynia, hypertension (it is better to a female having a complication of perneuralgia, rheumatoid arthritis with hypertension), itching due to skin eczema, and neurotic uterine contraction.

*Angelica gigas* prevents from losing one's hair or having gray hair by working on the brain, drawing energy downward and running blood to the head. Such *Angelica gigas* are used as a neutralizer or antidote when decocting medicinal herbs.

*Coix lachryma-jobi* is effective in all cancers such as gastric cancer, uterine cancer, breast cancer, esophageal cancer, lung cancer, laryngeal cancer, tongue cancer, skin cancer, renal cancer, bladder cancer or prostate cancer. *Coix lachryma-jobi* acclimatizes the stomach, helps the bowel, cleans the lung, and removes phlegm fen shui disease. Taking a dose for long goes vitality smoothly, feels lighter and is in good health. Particularly, this treats skin diseases such as acne and is effective in neuralgia.

*Saliconia herbacea* has excellent effects in removing coprostasis and in treating obesity. Also, this has a good pharmacological effect in hypertension and hypotension, facilitates blood circulation, makes blood clean, strengthens blood vessels, and thus treats hypertension and hypotension concurrently. Further, this is effective in empyema, sinusitis, nephritis and arthritis. *Saliconia herbacea* has a function to treat purulent inflammation and kill various bacteria and thus, it treats dropsy due to inflammation and arthritis. *Saliconia herbacea* has excellent effects in skin beauty care so that it calls an eating cosmetic. Taking *Saliconia herbacea* to remove coprostasis, the skin is surprisingly cleaned, and chloasma, freckle and acne are treated in most cases. Further, it improves the gastrointestinal function. *Saliconia herbacea* activates the function of intestine, facilitates gastrointestinal function and treats constipation, coprostasis, proctoptosis and hemorrhoid. This is effective in hypothyroidism, hyperthyroidism and diabetes. This allows to normalize the blood glucose level and to treat bronchial asthma. *Saliconia herbacea* has a function to recover bronchial mucosa and to relieve or treat bronchial asthma.

*Plantago asiatica* contains plantenolic acid, adenine, pholin and the like. This is more effective than ginseng or deer antlers and has anti-cancer effect. Leaf and stem of *Plantago asiatica* contains a substance for diuretic action. Thus, in order to treat habitual constipation, *Plantago asiatica* dried at sunshine is decocted and drunk. Raw leaf may be eaten as a green vegetable juice and it may be trampled to which hot water is added and then drunk instead of tea. Outguard or seed contains an ingredient of removing phlegm. As such, when bronchial asthma or phlegm do not stop, 15 to 20 g per day is decocted and drunk between meals. Even when adema results from nephritis, salt adsorption is reduced and seed is decocted and drunk in an amount of 5 to 15 g per day. This is effective in alleviation, diuresis, stethocatharsis, anti-bacterial, anti-inflammation, anti-cancer, icterus, paristhmion, hemostasis and furunculus.

*Achillea sibirica* has sthenia action, blood circulation facilitation action, strong hemostasis action, bacteriocidal action, anti-inflammatory action and antiallergic action. This is effective in hemorrhoid, contusion, sore spot due neuralgia, furuncle, several bleeding and gastric ulcer, hypertension, toothache, small and large intestine inflammation, anorexia, when bitten by poisonous snake, all acute and chronic inflammation, as well as in strong hemostasis and inflammation actions, and anti-allergic action.

*Rumex crispus* has a bitter taste and a cold property and is slightly poisonous. The root contains acetic acid. As such, a large dose should not be eaten at a time. This has functions to lower heat, to facilitate urine and feces, to kill parasites, to stop bleeding and to kill various bacteria. Tearing leaf and attaching it to the place where the wound is not yet healed or it is festered, is very effective. Making and applying a raw root as juice, or drying a raw root, powdering it, mixing the powder with vinegar and applying the mixture to a lesion are very effective in head skin disease, psoriasis, eczema, genital eczema, skin itching, or scabies. In the case of diseases called vitiligo vulgaris or vitligo and producing white spot on the skin, the root is deeply decocted and applied to a lesion. Water decocted by the root is effective in stopping uterine bleeding or nasal bleeding. Further, this is effective in vomiting, diarrhea, indigestion, acute and chronic pancreatitis, constipation, lymphadenitis, tonsillitis, gastritis, gastric ulcer, and stomach cancer.

*Rhododendron brachycarpum* is a medical herb which has good effects in all diseases. It is not mostly used in oriental medicine, but it is known as panacea for people which undergo disciple in mountain. *Rhododendron brachycarpum* is effective in treating or improving various diseases such as hypertension, hypotension, diabetes, neuralgia, arthritis, headache, menstrual irregularity, infertility, exhilaration deficiency, kidney disease, heart failure, obesity, athletes foot, liver cirrhosis, hepatitis, empyema, and otitis media. Further, *Rhododendron brachycarpum* has a special efficacy in vitiligo vulgaris.

*Lithospermum erythrorhizon* has a cold drug effect. This has excellent effects to lower a fever, cure a poison, remove an inflammation and make a granulation. This is effective in various cancers, constipation, liver disease, arteriosclerosis, female cold leucorrhoea, and menstrual irregularity. Taking a dose for long, it looks well and is not aged. *Lithospermum erythrorhizon* is used as anti-cancer in China. The long aged *Lithospermum erythrorhizon* in folk remedies is recognized as a mysterious herb comparable to a wild ginseng.

The binominal names of medicinal herbs used in the present invention can be represented as follows: *Zizania latifolia, Artemisia capillaries, Houttuynia cordata, Saururus chinensis, Leonurus sibiricus, Angelica gigas, Coix lachryma-jobi, Plantago asiatica, Rhododendron brachycarpum, Saliconia herbacea, Achillea sibirica, Rumex crispus, Lithospermum erythrorhizon*.

Further, the present invention relates to a process for preparing a composition for bath additives comprising: preparing medicinal herb materials comprising 10 to 25% by weight of *Zizania latifolia*, 10 to 20% by weight of *Artemisia capillaries*, 5 to 15% by weight of *Houttuynia cordata*, 1 to 20% by weight of *Saururus chinensis*, 1 to 15% by weight of *Leonurus sibiricus*, 1 to 15% by weight of *Angelica gigas*, 1 to 15% by weight of *Coix lachryma-jobi*, 1 to 10% by weight of *Plantago asiatica* and 1 to 10% by weight of *Rhododendron brachycarpum*, based on the total dry weight of the above herb materials; mixing the resulting herb materials, water and *Bacillus subtilis* which is anaerobic, and separating the mixture to a liquid phase fermentation at a temperature of 30 to 40° C. for 50 to 100 days; and separating sludge from the culture obtained from the liquid phase fermentation, drying, sterilizing and pulverizing the sludge.

The above descriptions with regard to the composition for bath additives are likewise applied to the above method for preparation. The method for preparation described below can be likewise applied to the above composition for bath additives.

In the liquid phase fermentation of the above method for preparation, the above medicinal herb materials, water and *Bacillus subtilis* which is anaerobic, can be mixed, but are not limited to, in a weight ratio of 2 to 7:85 to 93:0.2 to 10. That is, if the above mixing ratio is enough for the above medicinal herb to ferment through liquid phase fermentation for 50 to 100 days, it can be applied to a different ratio.

The anaerobic microorganism in the present invention uses preferably that which is in a vigorous state of metabolism action.

In the step of preparing the medicinal herb, the above herb may further comprise 1 to 10% by weight of *Saliconia herbacea,* 7 to 17% by weight of *Achillea sibirica,* 5 to 15% by weight of *Rumex crispus,* and 1 to 10% by weight of *Lithospermum erythrorhizon,* based on the total dry weight of the above herb materials.

Further, the present invention provides a process for preparing a composition for bath additives comprising:

separating sludge from the culture obtained from the above mentioned liquid phase fermentation, drying, sterilizing and pulverizing the culture to give a pulverized sludge; subsequently, mixing the above pulverized sludge with the second medicinal herb materials comprising 10 to 15% by weight of *Zizania latifolia,* 1 to 10% by weight of *Artemisia capillaries,* 1 to 10% by weight of *Houttuynia cordata,* 5 to 15% by weight of *Saururus chinensis,* 5 to 15% by weight of *Leonurus sibiricus,* 1 to 10% by weight of *Angelica gigas,* 3 to 12% by weight of *Coix lachryma-jobi,* 5 to 15% by weight of *Saliconia herbacea,* 1 to 10% by weight of *Plantago asiatica,* 5 to 15% by weight of *Achillea sibirica,* 5 to 15% by weight of *Rumex crispus,* 1 to 10% by weight of *Rhododendron brachycarpum* and 1 to 5% by weight of *Lithospermum erythrorhizon,* based on the total dry weight of the above herb materials, in a weight ratio of 3:7 to 7:3, the second materials provided in a powder state to prepare a mixture; and subjecting the mixture, water and *Aspergillus oryzae* which is leaven bacteria and *Lactobacillus acidophilus* which is lactic acid bacteria, to liquid phase fermentation at a temperature of 26 to 30° C. for 50 to 70 days.

In the liquid phase fermentation of the above method for preparation, a mixture of the above pulverized sludge and the second medicinal herb, a water, *Aspergillus oryzae* which is leaven bacteria and *Lactobacillus acidophilus* which is lactic acid bacteria, can be mixed, but are not limited to, in a weight ratio of 2 to 7:85 to 93:0.5 to 12. That is, if the above mixing ratio is enough for the above medicinal herb to ferment through liquid phase fermentation for 50 to 70 days, it can be applied to a different ratio.

*Aspergillus oryzae* which is leaven bacteria and *Lactobacillus acidophilus* which is lactic acid bacteria, can be mixed in a ratio of 1:9 to 9:1, based on the number of individual.

The efficacy of the composition for bath additives according to the present invention results from an activation of a natural healing power using a principle of human body. That is, the present composition provides an excellent body type correction effect in accordance with a principle of muscular relaxation action. The organ, tissue and cell (smallest unit) of human body are activated, respectively, by a natural detoxifying and purifying action (DITOX) and an immunological enhancement action in the human body. Therefore, the self repair system of human body is repaired to lead to a spontaneous natural healing effect.

The natural DITOX action of the composition for bath additives according to the present invention results from a microorganism energy wave therapy. Toxin (active oxygen, etc.) in the body is discharged by a natural healing therapy rather than water or operation. When detoxifying a human body with the composition for bath additives according to the present invention, the human body is renewed as a clean body to have a balance and also the function of immune system is improved.

BEST MODE FOR CARRYING OUT INVENTION

Hereinafter, the present invention is described in more detail with reference to examples. However, the following examples are intended to illustrate the invention, and the scope of the invention is not limited to these examples. The examples can be properly corrected and modified by a person skilled in the art within the scope of the present invention.

Example 1

Preparation of the Composition for Bath Additives

In a fermentation chamber, 0.5 ton of water was placed. 20 kg of dried medicinal herb materials wherein 15% by weight of *Zizania latifolia,* 15% by weight of Artemisia capillaries, 10% by weight of *Houttuynia cordata,* 15% by weight of Saururus chinensis, 10% by weight of *Leonurus sibiricus,* 10% by weight of *Angelica gigas,* 10% by weight of *Coix lachryma-jobi,* 5% by weight of Plantago asiatica and 5% by weight of *Rhododendron brachycarpum* were mixed, were added and then 5 kg of *Bacillus subtilis,* anaerobic microorganism, was added. The internal temperature of the fermentation chamber was adjusted to 36° C. and cultured for 60 days. The culture solution was removed from the culture. Sludge was separated, dried and then finely pulverized to prepare the composition for bath additives.

Example 2

Preparation of the Composition for Bath Additives

In a fermentation chamber, 0.5 ton of water was placed. 20 kg of dried medicinal herb materials wherein 15% by weight of *Zizania latifolia,* 15% by weight of *Artemisia capillaries,* 10% by weight of *Houttuynia cordata,* 3% by weight of *Saururus chinensis,* 5% by weight of *Leonurus sibiricus,* 5% by weight of *Angelica gigas,* 5% by weight of *Coix lachryma-jobi,* 5% by weight of *Saliconia herbacea,* 5% by weight of *Plantago asiatica,* 12% by weight of *Achillea sibirica,* 10% by weight of *Rumex crispus,* 5% by weight of *Rhododendron brachycarpum* and 5% by weight of *Lithospermum erythrorhizon* were mixed, were added and then 10 kg of *Bacillus subtilis,* anaerobic microorganism, was added. The internal temperature of the fermentation chamber was adjusted to 36° C. and cultured for 90 days. The culture solution was removed from the culture. Sludge was separated, dried and then finely pulverized to prepare the composition for bath additives.

Example 3

Preparation of the Composition for Bath Additives

In a fermentation chamber, 0.5 ton of water was placed. 15 kg of the composition for bath additives obtained from Example 2, 15 kg of dried medicinal herb materials wherein 10% by weight of *Zizania latifolia,* 5% by weight of *Artemisia capillaries,* 5% by weight of *Houttuynia cordata,* 10% by weight of *Saururus chinensis,* 10% by weight of *Leonurus sibiricus,* 5% by weight of Angelica gigas, 10% by weight of *Coix lachryma-jobi,* 10% by weight of *Saliconia herbacea,* 5% by weight of *Plantago asiatica,* 10% by weight of *Achillea sibirica,* 10% by weight of *Rumex crispus,* 5% by weight of *Rhododendron brachycarpum* and 5% by weight of *Lithospermum erythrorhizon* were mixed, were added and then 15 kg of *Aspergillus oryzae,* leaven bacteria, and 15 kg of *Lactobacillus acidophilus,* lactic acid bacteria, were added. The internal temperature of the fermentation chamber was adjusted to 28° C. and cultured for 60 days. The culture solution was removed from the culture. Sludge was separated, dried and then finely pulverized to prepare the composition for bath additives Test Example Clinical Evaluation about Efficacy of the Composition for Bath Additives 20 kg of the respective composition for bath additives obtained from Examples 1 to 3 was placed in the bath labeled as number of respective examples. The temperature of bath water was adjusted to 39° C., and each subject entered a bath room and bathed for 40 minutes to 1 hour at one time. Bathing was performed from one time to ten times depending on the conditions of each subject.

To total 1000 clinical subjects (teenage: 60, the twenties: 70, the thirties to the sixties: 870, male: 200, female: 800), bathing was continuously performed. Specifically, 333 persons in a bath water using the composition for bath additives of Example 1, 333 persons in a bath water using the composition for bath additives of Example 2, and 334 persons in a bath water using the composition for bath additives of Example 3, have taken a bath up to the number required.

As a result of the test, there was a difference depending on sex, injure level of body, age and the like, but in common the body type correction and immunological enhancement effects were clearly confirmed by statistics. Further, the body function recovery due to a natural detoxifying action and the skin resilience improvement increasing a beauty care were clearly confirmed, and other effects were also confirmed.

Specifically, the body type correction effect was confirmed in 96% of the subject, the body function improvement was confirmed in 90% of the subject, and the muscular problem was improved in 100% of the subject.

(1) Improvement of Scoliosis, Gibbosity and Ithylordosis

From 980 subjects having conditions of scoliosis, gibbosity and ithylordosis, it was confirmed that the conditions were very improved. The reason why such conditions were improved by in a bath therapy using the composition for bath additives of the present invention are considered to result from a change of body due to a muscular relaxation. That is, the change of body due to a muscular relaxation can be represented in the following order:

Muscular relaxation→facial relaxation surrounding the muscle→nerve→erector spine muscle→vertebral system Therefore, the vertebral system is eventually recovered into its originally healthy state by such sequential change.

Figure 1:
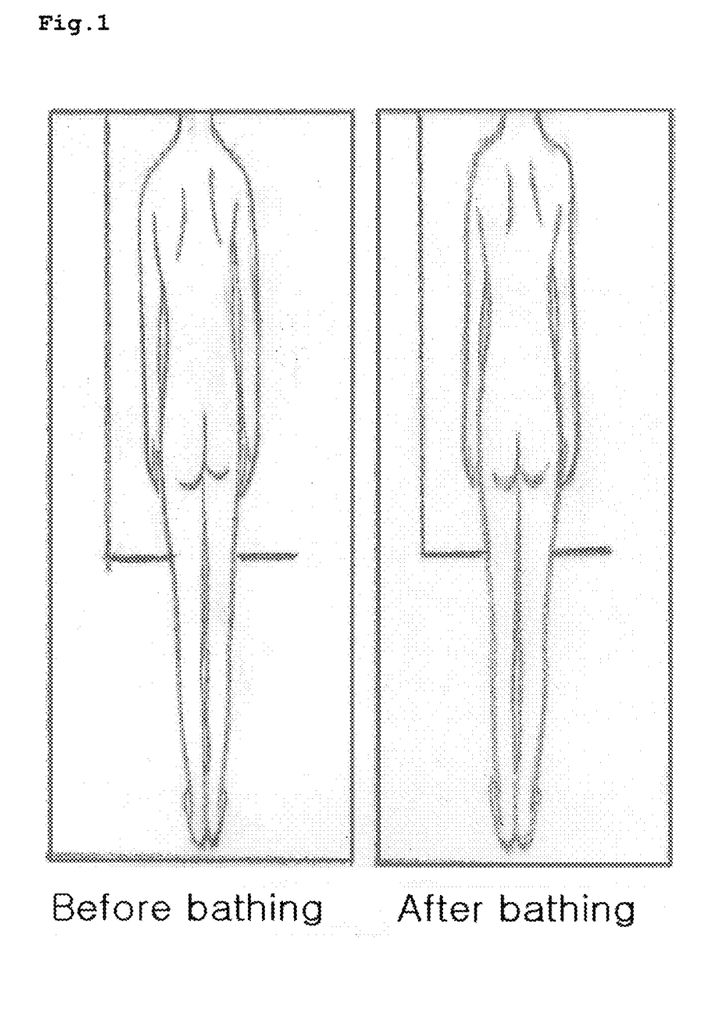
FIGS. 1 to 3 are pictures showing a body type correction effect of a clinical subject wherein the bathing is carried out with the composition for bath additives described in Example 3 of the present application at one time for one hour.
Figure 2:
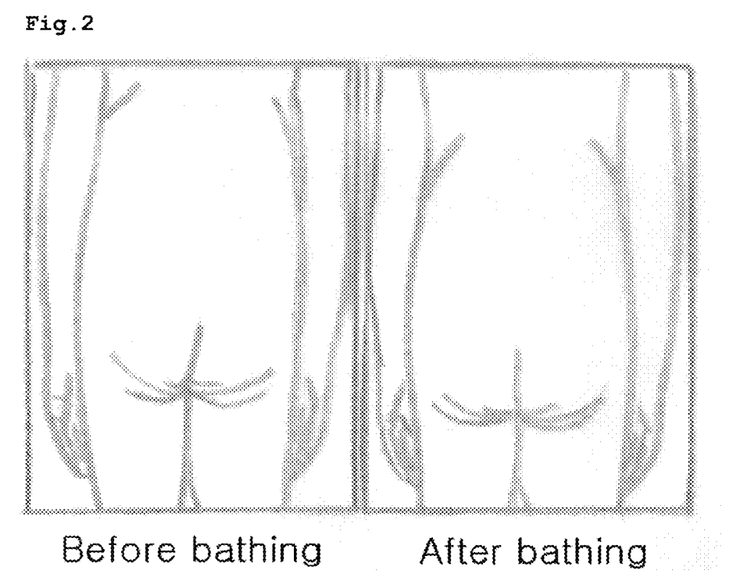
Figure 3:
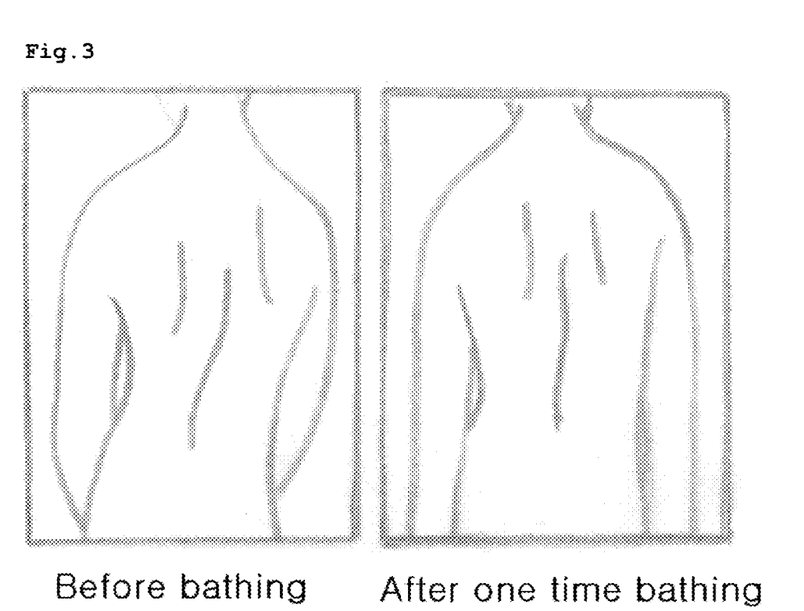

FIGS. 1 and 2 are pictures showing clinical cases wherein the batching is carried out with the composition for bath additives described in Example 3 of the present application at one time. As are seen by Figures, a crooked skeleton is straightened by taking a bath with the composition for bath additives according to the present invention (2) Clinical Reaction of Teenage (a) Whole Clinical Result In the teenage of the clinical subjects, there were many cases where a balance of body was collapsed due to the non-straightened poster and chronic stress. However, the teenage has excellent regeneration properties of the body and thus, it has been shown that the body type correction effect was very excellent even in a short time. Further the function improvement effect of whole body has also been confirmed.

(b) Specific Clinical Cases

Age, sex and occupation: sixteen, female, student

Condition: Chronic scoliosis

Number of bathing: 10

For the above clinical subjects, a change of spine was initiated a little from the first grade of middle school, but they had no regard and were not inconvenienced, thus, they did not mind. Eventually, the spine of the clinical subjects was injured as much as operation was required. In an attempt to avoid the operation, they participated in clinical test of the bath additives of the present invention.

As a result of clinical test, it has been shown that the body type correction effect was very excellent irrespective of only one time bath therapy. As the number of bathing was increased, the effect of spine correction was increased. At the time of performing ten times bath therapy, a spine correction effect has been shown to be not perfect, but considerable.

(3) Clinical Reaction of the Twenties to the Thirties (a) Whole Clinical Result

More than 80% of the clinical subjects of the twenties to the thirties have conditions such as tonic omodynia and neck muscular conglomerate resulting from mental stress during a work life, a school life, marriage or early pregnancy, gastrointestinal disturbance due to irregular meals, and unbalance due to chronic fatigue. 150 female subjects have suffered from dysmenorrheal, but almost all conditions have been improved by bathing with the composition for bath additives according to the present invention.

(b) Specific Clinical Cases (Change of Body and Skin Appeared Before and after Clinical Test)

Age, sex and occupation: 25, female, company staff

Number of bathing: 10

Conditions: Stress chronic enterogastritis, reflux oesophagitis, hyperchylia and gastroptosis Clinical subjects were sensitive and diagnosed as a stress enterogatritis from hospital due to irregular meals and stress. Only when they have conditions without continued treatment, they took a drug and stood for a long time. As such, gastric retention, hyperchylia and gastroptosis were very severe.

As a result of clinical test, it has been shown that when one time bath therapy was performed, the subject has complained of nausea, vomiting and dizziness while touching stomach. During such reaction, while the component wave of the present invention was applied to a human body, it was touched from the weakest portion of human body and returned to a state when they were healthy. When the number of bathing was more than three times, the clinical subjects started to feel a little convenience. As the number of bathing was increased close to 10 times, the reflux oesophagitis was improved a little and the mental anxiety was improved.

(4) Clinical Reaction of More than the Forties (a) Whole Clinical Result

The human body is rapidly aged from the forties. Therefore, they have to pay attention to their health. Specific conditions appearing from the forties or more include omodynia due to chronic stress, function lowering of immune system, cell aging, skeleton system trouble, function lowering of muscle including a nervous system, a muscle weakness due to a lack of exercise, and a blood circulation disorder.

The above conditions were mainly checked. As a result, it has been confirmed that asymmetry of skeleton, asymmetry of hipline, problem of pelvic front region and pelvic posterior region, mutation of cell, problem of skin tag or colloid milium, problems of stagnant five viscera and six entrails have been alleviated, improved and recovered.

(b) Specific Clinical Cases

Age, sex and occupation: 52, female, business

Number of clinical test: 10

Conditions: The subjects have many knee wrinkles, and uneven body line by a similar phenomenon to edema due to waste in the body, and are under chronic fatigue and inflamed eye. The above uneven body line has been considered to be formed by having an influence on respective body organ or blood or other region after toxin to be discharged is stagnant as it stands. The above chronic fatigue seemed to result from lowering of liver function. As such, it has been considered that eyes were inflamed.

As result of clinical test, it has been confirmed that knee wrinkles were significantly reduced by muscle potentiation through one or two times body bath therapy. It could be seen that fatigue and inflammation of eye have been significantly improved. Such effects have been considered that liver detoxifying was made by a natural healing principle. It could be confirmed that a body line was greatly improved when 10 times bath therapies were performed.

(c) Specific Clinical Cases

Age, sex and occupation: 53, male, singer

Conditions: skin pigmentation due to toxin in the body, dyspepsia and chronic fatigue feeling Number of clinical test: 13

Conditions: Clinical subjects have a lot of facial blemishes and also composite skin tone. As a whole, the skin was not well cared and thus the first impression is not good.

As a result of clinical test, it could be confirmed that the skin tone was brightened a lot when one bath therapy was performed and that pigmentation, hair pouch contraction, and skin tag of neck portion have been improved from five times bath. In addition, it could be confirmed that dyspepsia and chronic fatigue have been improved.

What is claimed is:

1. A composition for bath additives, the composition obtained by:
    subjecting medicinal herb materials to liquid phase fermentation with *Bacillus subtilis* to obtain a culture, the herb materials comprising 10% to 25% by weight of *Zizania latifolia*, 10% to 20% by weight of *Artemisia capillaries*, 5% to 15% by weight of *Houttuynia cordata*, 1% to 20% by weight of *Saururus chinensis*, 1% to 15% by weight of *Leonurus sibiricus*, 1% to 15% by weight of *Angelica gigas*, 1% to 15% by weight of *Coix lachryma-jobi*, 1% to 10% by weight of *Plantago asiatica* and 1% to 10% by weight of *Rhododendron brachycarpum*, based on a total dry weight of the herb materials;
    separating sludge from the culture; and
    drying, sterilizing and pulverizing the separated sludge.

2. The composition for bath additives as claimed in claim 1 wherein the liquid phase fermentation is performed at a temperature of 30° C. to 40° C. for 50 to 100 days.

3. The composition for bath additives as claimed in claim 1 wherein the medicinal herb materials further comprise 1% to 10% by weight of *Saliconia herbacea*, 7% to 17% by weight of *Achillea sibirica*, 5% to 15% by weight of *Rumex crispus*, and 1% to 10% by weight of *Lithospermum erythrorhizon*, based on total dry weight of the herb materials.

4. A composition for bath additives, wherein the composition is obtained by a process comprising:
    subjecting first medicinal herb materials to first liquid phase fermentation with *Bacillus subtilis* to obtain a first culture, the first medicinal herb materials comprising 10% to 25% by weight of *Zizania latifolia*, 10% to 20% by weight of *Artemisia capillaries*, 5% to 15% by weight of *Houttuynia cordata*, 1% to 20% by weight of *Saururus chinensis*, 1% to 15% by weight of *Leonurus sibiricus*, 1% to 15% by weight of *Angelica gigas*, 1% to 15% by weight of *Coix lachryma-jobi*, 1% to 10% by weight of *Plantago asiatica* and 1% to 10% by weight of *Rhododendron brachycarpum*, based on the total dry weight of the first medicinal herb materials;
    separating first sludge from the first culture;
    drying, sterilizing and pulverizing the separated sludge to obtain a first pulverized sludge;
    mixing the first pulverized sludge with second medicinal herb materials, the second medicinal herb materials comprising 10% to 15% by weight of *Zizania latifolia*, 1% to 10% by weight of *Artemisia capillaries*, 1% to 10% by weight of *Houttuynia cordata*, 5% to 15% by weight of *Saururus chinensis*, 5% to 15% by weight of *Leonurus sibiricus*, 1% to 10% by weight of *Angelica gigas*, 3% to 12% by weight of *Coix lachryma-jobi*, 5% to 15% by weight of *Saliconia herbacea*, 1% to 10% by weight of *Plantago asiatica*, 5% to 15% by weight of *Achillea sibirica*, 5% to 15% by weight of *Rumex crispus*, 1% to 10% by weight of *Rhododendron brachycarpum* and 1% to 5% by weight of *Lithospermum erythrorhizon*, based on the total dry weight of the second medicinal herb materials;
    subjecting the mixture to second liquid phase fermentation with *Aspergillus oryzae*, and *Lactobacillus acidophilus* to obtain a second culture; and
    separating second sludge from the second culture and drying the separated second sludge.

5. The composition for bath additives as claimed in claim 4 wherein the first liquid phase fermentation is performed at a temperature of 30° C. to 40° C. for 50 to 100 days, and the second liquid phase fermentation is performed at a temperature of 26° C. to 30° C. for 50 to 70 days.

6. The composition for bath additives as claimed in claim 4 wherein the first medicinal herb materials further comprise 1% to 10% by weight of *Saliconia herbacea*, 1% to 17% by weight of *Achillea sibirica*, 5% to 15% by weight of *Rumex crispus*, and 1% to 10% by weight of *Lithospermum erythrorhizon*, based on the total dry weight of the first herb materials.

7. A process for preparing a composition for bath additives comprising:
    preparing first medicinal herb materials comprising 10% to 25% by weight of *Zizania latifolia*, 10% to 20% by weight of *Artemisia capillaries*, 5% to 15% by weight of *Houttuynia cordata*, 1% to 20% by weight of *Saururus chinensis*, 1% to 15% by weight of *Leonurus sibiricus*, 1% to 15% by weight of *Angelica gigas*, 1% to 15% by weight of *Coix lachryma-jobi*, 1% to 10% by weight of *Plantago asiatica* and 1% to 10% by weight of *Rhododendron brachycarpum*, based on the total dry weight of the first medicinal herb materials;
    mixing the first medicinal herb materials, water and *Bacillus subtilis* to obtain a first mixture;
    subjecting the first mixture to a first liquid phase fermentation at a temperature of 30° C. to 40° C. for 50 to 100 days, to obtain a first culture;
    separating first sludge from the first culture; and
    drying, sterilizing and pulverizing the first separated sludge to obtain a first pulverized sludge.

8. The process as claimed in claim 7 wherein, the first medicinal herb materials further comprise 1% to 10% by weight of *Saliconia herbacea*, 1% to 17% by weight of *Achillea sibirica*, 5% to 15% by weight of *Rumex crispus*, and 1% to 10% by weight of *Lithospermum erythrorhizon*, based on total dry weight of the first medicinal herb materials.

9. The process of claim 7 further comprising:
    mixing the first pulverized sludge with second medicinal herb materials comprising 10% to 15% by weight of *Zizania latifolia*, 1% to 10% by weight of *Artemisia capillaries*, 1% to 10% by weight of *Houttuynia cordata*, 5% to 15% by weight of *Saururus chinensis*, 5% to 15% by weight of *Leonurus sibiricus*, 1% to 10% by weight of *Angelica gigas*, 3% to 12% by weight of *Coix lachryma-jobi*, 5% to 15% by weight of *Saliconia herbacea*, 1% to 10% by weight of *Plantago asiatica*, 5% to 15% by weight of *Achillea sibirica*, 5% to 15% by weight of *Rumex crispus*, 1% to 10% by weight of *Rhododendron brachycarpum* and 1% to 5% by weight of *Lithospermum erythrorhizon*, based on total dry weight of the second medicinal herb materials, to obtain a second mixture;

mixing the second mixture, water and *Aspergillus oryzae* and *Lactobacillus acidophilus* to obtain a third mixture; and subjecting the third mixture to a second *liquid phase fermentation* liquid phase fermentation at a temperature of 26° C. to 30° C. for 50 to 70 days.

* * * * *